United States Patent
Krill et al.

(10) Patent No.: US 10,125,077 B2
(45) Date of Patent: Nov. 13, 2018

(54) OPTIMIZED PROCESS FOR PREPARING METHACRYLIC ACID

(71) Applicants: Steffen Krill, Muehltal (DE); Rudolf Burghardt, Darmstadt (DE); Melanie Raczek, Darmstadt (DE); Torsten Balduf, Pfungstadt (DE)

(72) Inventors: Steffen Krill, Muehltal (DE); Rudolf Burghardt, Darmstadt (DE); Melanie Raczek, Darmstadt (DE); Torsten Balduf, Pfungstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 15/515,682

(22) PCT Filed: Nov. 16, 2015

(86) PCT No.: PCT/EP2015/076667
§ 371 (c)(1),
(2) Date: Mar. 30, 2017

(87) PCT Pub. No.: WO2016/079044
PCT Pub. Date: May 26, 2016

(65) Prior Publication Data
US 2017/0305830 A1    Oct. 26, 2017

(30) Foreign Application Priority Data

Nov. 19, 2014    (EP) .................................... 14193871

(51) Int. Cl.
| | | |
|---|---|---|
| *C07C 57/02* | (2006.01) | |
| *C07C 57/04* | (2006.01) | |
| *C07C 45/75* | (2006.01) | |
| *C07C 51/25* | (2006.01) | |
| *C07C 51/48* | (2006.01) | |
| *B01D 3/14* | (2006.01) | |
| *B01D 69/02* | (2006.01) | |
| *B01J 19/18* | (2006.01) | |
| *C07C 51/235* | (2006.01) | |
| *C07C 47/04* | (2006.01) | |
| *C07C 47/22* | (2006.01) | |

(52) U.S. Cl.
CPC ............... *C07C 57/04* (2013.01); *B01D 3/14* (2013.01); *B01D 69/02* (2013.01); *B01J 19/1818* (2013.01); *C07C 45/75* (2013.01); *C07C 51/235* (2013.01); *C07C 51/252* (2013.01); *C07C 51/48* (2013.01); *C07C 47/04* (2013.01); *C07C 47/22* (2013.01)

(58) Field of Classification Search
CPC ......... C07C 47/22; C07C 57/04; C07C 45/75; C07C 51/235; C07C 51/252; C07C 51/48; B01D 3/14; B01D 69/02; B01J 19/1818; B01J 27/053; B01J 31/0209; B01J 31/0237

See application file for complete search history.

(56) References Cited

U.S. PATENT DOCUMENTS

| | | | | |
|---|---|---|---|---|
| 4,408,079 A | * | 10/1983 | Merger | ................... C07C 45/75 568/461 |
| 4,496,770 A | * | 1/1985 | Duembgen | ............. C07C 45/75 568/461 |
| 2014/0206831 A1 | | 7/2014 | Venkitasubramanian | |

FOREIGN PATENT DOCUMENTS

| | | | |
|---|---|---|---|
| DE | 3844087 | * | 7/1990 |
| EP | 0 194 620 A2 | | 9/1986 |
| EP | 0 194 620 A3 | | 9/1986 |
| WO | 2012/154450 A2 | | 11/2012 |
| WO | 2012/154450 A3 | | 11/2012 |

OTHER PUBLICATIONS

DE3844087 translated 4 pages (Year: 1990).*
International Search Report dated Jan. 25, 2016 in PCT/EP2015/076667 filed Nov. 16, 2015.
European Search Report dated May 29, 2015 in European Application 14193871.2 filed Nov. 19, 2014.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to an optimized process for preparing methacrylic acid, wherein methacrolein is prepared in a first stage from propionaldehyde and formaldehyde by means of a Mannich reaction and oxidized in a second stage to methacrylic acid. More particularly, the present invention relates to the reduction in the amounts of catalyst to be used in the first stage, especially to the reduction in the amounts of acid to be used here, by virtue of the additional installation of recycling streams suitable for the purpose.

15 Claims, No Drawings

OPTIMIZED PROCESS FOR PREPARING METHACRYLIC ACID

The present invention relates to an optimized process for preparing methacrylic acid, wherein methacrolein is prepared in a first stage from propionaldehyde and formaldehyde by means of a Mannich reaction and oxidized in a second stage to methacrylic acid. More particularly, the present invention relates to the reduction in the amounts of catalyst to be used in the first stage, especially to the reduction in the amounts of acid to be used here, by virtue of the additional installation of recycling streams suitable for the purpose.

PRIOR ART

There exists a great interest in very simple, economically viable and environmentally friendly preparation processes for methacrylic acid. At the same time, there is particular interest in a process for preparing methacrylic acid on the basis of $C_2$ units. In this process, for example, propionaldehyde is prepared in a precursor from ethylene, carbon monoxide and hydrogen and is then reacted by means of a Mannich-like reaction with formaldehyde to give methacrolein. This Mannich reaction is generally catalysed with a combination of bases and acids. In a further stage, referred to hereinafter as process step 2, this methacrolein is then oxidized to methacrylic acid, for example in a directly connected plant. Esterification to methyl methacrylate, for example, may follow in further conversion steps.

A problem with this methacrylic acid synthesis is that large amounts of catalyst are consumed in the Mannich reaction, referred to hereinafter as process step 1. There is therefore a great economic interest in reducing the amount of catalyst to be used.

Details of the $C_2$ process for preparing methacrolein can be found, inter alia, in the publications U.S. Pat. Nos. 7,141,702, 4,408,079, JP 3069420, JP 4173757, EP 0 317 909 and U.S. Pat. No. 2,848,499.

The processes which are based on a Mannich reaction and are suitable for preparation of methacrolein are the subject of corresponding review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2.

EP 0 194 620 discloses a corresponding combination of process steps 1 and 2, without addressing the catalyst concentrations in process step 1 in any way.

DE 3213681 describes a process for preparing MAL, which is especially characterized in that the reaction is conducted at a temperature of greater than 150° C. with a reaction time of not more than 25 min in the presence of secondary amines and optionally of acids. In this process, based on 1 mol of propionaldehyde, between 0.001 and 0.25 and especially between 0.02 and 0.05 mol of a secondary amine as base and between 0 and 0.25 and especially between 0.02 and 0.05 mol of an acid are used. These are fed to the reactor exclusively in fresh form and, after the reaction, are separated from the methacrolein and disposed of with the aqueous phase.

U.S. Pat. No. 4,408,079 describes a process for preparing MAL in which the reaction of propionaldehyde with formalin is conducted at a molar ratio of 0.9 to 1.5:1, a pH between 2.5 and 7 and temperatures of 0° C. to 150° C. in the presence of a secondary amine, in a concentration of 0.025 to 0.75 or of 0.05 to 1.5 mol, and organic acids at a concentration of 0.05 to 1.5 mol, based in each case on 1 mol of propionaldehyde. U.S. Pat. No. 4,408,079 also describes exclusively fresh supply of the catalyst components and removal and disposal after the reaction.

PROBLEM

In view of the prior art, the problem addressed by the present invention was therefore that of providing a process for preparing methacrylic acid in combination with the synthesis of methacrolein (MAL) by the $C_2$ process in a first process step, in which only a reduced amount of catalysts overall has to be added in the first process step compared to the prior art.

More particularly, the problem was thus that of using this process to be able to prepare an MAL as a precursor in the synthesis of methacrylic acid, which can be conducted with addition of less fresh acid at identical yields and selectivities compared to the prior art.

In addition, the problem was that of providing a process for preparing methacrylic acid, consisting of the synthesis of MAL by means of a Mannich reaction in the first process step and the subsequent oxidation of MAL to methacrylic acid in a second process step, in which the overall yield of methacrylic acid can be increased compared to the prior art.

Further objects not mentioned explicitly will become apparent from the overall context of the following description and the claims.

SOLUTION

The problems underlying this invention are solved by means of a novel process for continuously preparing methacrylic acid, in which methacrolein is prepared in a first process step from formaldehyde and propionaldehyde with at least one acid and at least one organic base as catalysts in a reactor 1, then separated from the catalyst-containing or aqueous phase present and oxidized in a second process step to methacrylic acid with a heterogeneous catalyst in the presence of oxygen and water in a reactor 2. The first process step is a Mannich reaction.

The process gas formed in process step 2, after being led out of the reactor 2, is condensed and quenched to produce an aqueous crude methacrylic acid. This is followed by the separation of the methacrylic acid from the aqueous phase with an extractant. This extractant is generally an organic solvent having only low water miscibility and a low boiling point. Examples of these are alkanes or mixtures thereof, for example hexane or pentane in particular.

According to the invention, the aqueous phase from the organic phase containing the methacrylic acid, after being extracted, is passed wholly or partly, directly or indirectly, into reactor 1. This aqueous phase especially comprises carboxylic acids. These carboxylic acids then act as one of the two catalyst components in reactor 1 during the Mannich reaction of process step 1 and it is no longer necessary to pass—after the general reaction equilibrium has been established—as much, if any, fresh acid into reactor 1.

The organic base is preferably a secondary amine, more preferably dimethylamine. The acid which is fed fresh to reactor 1 at least on startup of the continuous reaction and usually also to a reduced degree in the case of a continuous mode of operation may be an organic or inorganic acid. It is preferably sulphuric acid or an organic acid, especially formic acid, acetic acid, propionic acid and/or mixtures of these acids, and it is also possible to use mixtures of two or more acids.

The carboxylic acids that are present in the aqueous phase and are passed in accordance with the invention from process step 2 directly or indirectly into reactor 1 are especially acetic acid, methacrylic acid, propionic acid, maleic acid, acrylic acid, terephthalic acid. In general, the acids are especially mixtures comprising at least one of these acids, and it is usually the case that all these acids are present in the mixture in the procedure, and further acids which are formed as by-product of the oxidation in process step 2 or are transferred as well into reactor 2 as a by-product in the MAL from process step 1. In this case, the ratios of the individual acids to one another depend especially on the process parameters of process step 2. Thus, the content of propionic acid or terephthalic acid in particular may be relatively small, or they may be present in concentrations at the detection limit. Methacrylic acid, in contrast, remains in the aqueous phase in small amounts in the extraction and is thus always present.

It is a characteristic feature that these acids form during the oxidation of the methacrolein and are passed into reactor 1 as a mixture with the product water from the oxidation.

As well as the acids mentioned, the aqueous phase passed into reactor 1 may also comprise further acids in a very small concentration. Examples of these are isophthalic acid, benzoic acid, 4-methylbenzoic acid or the oxidation product of a dimeric methacrolein.

In addition, the wastewater may comprise formaldehyde. This formaldehyde is formed as a by-product mainly in reactor 2 in the oxidation. The content of the aqueous phase which is fed directly or indirectly to reactor 1 may especially be between 0.2% and 1.0% by weight. Formaldehyde, however, is especially a reactant in the methacrolein synthesis in reactor 1. Thus, it is a further surprising aspect of the present invention that not just the total use amount of the catalyst acids can be reduced for the reaction in reactor 1, but it is also necessary to feed somewhat less fresh formaldehyde into reactor 1, since a portion of this formaldehyde can likewise be recycled into reactor 1. Further intermediate processing of the recycling stream does not constitute any problems here either, since formaldehyde is retained for the most part by means of a membrane, for example, and thus remains in the recycling stream.

Formaldehyde-containing wastewaters additionally have the great disadvantage that no biological workup is available therefor. Thus, the formaldehyde content in the wastewater is the primary reason why it has to be sent to incineration. The process according to the invention with full or partial recycling of the aqueous phase after process step 2 now makes it possible to distinctly reduce the amount of formaldehyde emitted in the liquid phase. It is thus possible to conduct the overall process with much smaller amounts to be fed to incineration, or entirely without a thermal disposal.

As well as the smaller use amounts of acids in process step 1, a further advantage of the present invention is thus considered to be that the methacrylic acid remaining in the aqueous phase from the extraction which follows on from process step 2 is passed wholly or at least partly into reactor 1 and transferred thence back into reactor 2 together with the MAL. Thus, this methacrylic acid which is actually lost according to the prior art is available for a new extraction and the methacrylic acid yield of the overall reaction is increased by up to 1% by weight compared to the prior art.

More particularly, in accordance with the invention, at least 5% by weight, preferably at least 20% by weight and more preferably at least 50% by weight of the acid fed into reactor 1 as catalyst is the carboxylic acids from process step 2. In the case of optimization of the process, it may even be possible to operate process step 1 entirely without supply of fresh acid after the equilibrium has been established. This proportion of recycled acid especially applies to a juncture after the attainment of a steady state in the continuous process.

According to the invention, the establishment of the equilibrium means that, in the continuous reaction, after the start-up of the reaction, a state is attained in process steps 1 and 2 in which the internal temperatures and the internal pressure of the reactors and the feed, recycling, transfer and removal streams in both reaction steps are subject to only very small variations of not more than 5° C., 2 bar or 5%. Feed streams are understood to mean streams with which reactants, solvents such as water, catalysts or further auxiliaries are fed in fresh form to reactor 1, reactor 2 or a column in one of the process steps.

Recycling streams are understood to mean streams with which reaction phases are passed back into an upstream reactor 1 or 2. These streams may, as well as the stream according to the invention comprising the aqueous solution of the carboxylic acids from process step 2 into reactor 1, also be, for example, the at least partial return of the bottoms from a downstream column into reactor 1. Transfer streams, in contrast, are streams which follow the actual course of the reaction. Examples of these are the efflux from reactor 1 into a downstream column or the feed of the MAL into reactor 2. The removal streams, in turn, are streams by means of which phases are finally removed from the system. As well as the product withdrawal, these streams may, for example, also be an offgas or the withdrawal of an aqueous phase, for example, for disposal.

In a particular embodiment of the present invention, the aqueous phase from process step 2, before being introduced into reactor 1, is concentrated by means of a distillation or a membrane separation stage. This execution has the great advantage that it is possible on the one hand to pass greater amounts of the acid into reactor 1, but the amount of the water transferred as well is comparatively small.

In a corresponding distillation, the acid-rich phases can be removed either in the remaining bottoms or in the column tops, or via one or more side streams. It is also possible to withdraw the acid-containing phases at a plurality of these points in the column and then to combine them again before they are passed into reactor 1.

Preferably and simultaneously independently of the other embodiment of the process according to the invention, the converted reaction solution from process step 1, after being withdrawn at the reactor exit, is distilled in a column. Subsequently, the methacrolein-containing phase withdrawn from the column is separated in a phase separation vessel into methacrolein and an aqueous phase. This aqueous phase can then be returned wholly or partly to the column. Generally connected upstream of this phase separator is a condenser for liquefaction of the top stream from the distillation column.

In an equally preferred alternative embodiment of the invention, the converted reaction solution from process step 1, after being withdrawn at the reactor exit, is distilled in a column. In this embodiment, the top stream of this distillation is then subsequently passed directly into reactor 2 without undertaking any intermediate phase separation.

Irrespective of the configuration with or without subsequent phase separation, it is particularly preferable to recycle a portion, especially at least 20% by weight of the aqueous phase from the column bottoms comprising acids and organic bases and the particular proportion of base in the salts with the acids and in the base-containing intermediates of process step 1 is recycled into the inlet of reactor 1. This stream is referred to hereinafter as recycling stream.

In a further, likewise preferred embodiment of the process according to the invention, the aqueous phase from process step 2 is passed wholly or partly into this column connected downstream of process step 1 and thence passed into reactor 1 at least partly together with the column bottoms in the above-described recycling stream. Optionally, the column bottoms before being introduced into reactor 1 can be concentrated by means of a further distillation or a membrane separation stage. This workup may be installed irrespective of whether or not the aqueous phase from process step 2 is passed into these bottoms.

Alternatively, and equally preferably, the aqueous phase from process step 2 is passed wholly or partly directly into reactor 1. In this case, it is possible, albeit less preferred, to install two separate membrane separation stages and/or distillations for this stream and the recycling stream from the column bottom.

A more preferred embodiment of the present process is one in which the aqueous phase from process step 2 after being extracted and before being introduced into reactor 1 is mixed with at least a portion of the bottoms from the column connected downstream of reactor 1, i.e. the recycling stream, and the mixture is optionally concentrated by means of a distillation or a membrane separation stage before this combined stream is passed into reactor 1.

In such a membrane separation stage, it is possible to use, for example, nanofiltration or reverse osmosis membranes suitable for separation of water from a mixture. Known for this purpose are membranes from the field of water treatment or water desalination, as otherwise used, for example, for production of drinking water or boiler feed water in power plants. Preference is given to membranes having a separation-active layer composed of polyamide, cellulose acetate or polyether sulphone, more preferably of a polyamide. An example of good suitability for the purpose is the Dow Filmtec SW30HR membrane.

In general, the membranes are in the form of spiral-wound elements. Details of the exact construction of such membranes can be found, for example, in Th. Melin, R. Rautenbach "Membranverfahren—Grundlagen der Modul—und Anlagenauslegung" [Membrane Methods—Principles of Module and System Design], 3rd edition, Springer Verlag, Berlin, p. 173-175.

The membrane separation stage can be operated, for example, at a local membrane temperature between 10 and 70° C., preferably between 30 and 40° C. The transmembrane pressure is, for example, between 20 and 100 bar, preferably between 70 and 90 bar. The exact system technology for inclusion of the membrane separation stages in such a production plant is known to those skilled in the art and details can be found, for example, in Th. Melin, R. Rautenbach "Membranverfahren—Grundlagen der Modul—und Anlagenauslegung", 3rd edition, Springer Verlag, Berlin, p. 205-226 and 245-308.

The process according to the invention comprises, in process step 1, the preparation of methacrolein by reaction of propanal with formaldehyde via an aldol or Mannich condensation. The formaldehyde can be used here, for example, in the form of formalin. The processes suitable for this purpose are known to those skilled in the art and are the subject of corresponding review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2. More particularly, reference should also be made to the particularly preferred version of this process step 1, as described in the European patent application having the reference number 13002076.1.

Preference is given to conducting the reaction in process step 1 at a temperature of 100 to 300° C., a residence time of the reaction mixture in reactor 1 between 1 and 30 s, more preferably between 5 and 15 s, and at a pressure of 5 to 100 bar. Preferably, the feed into reactor 1 has a ratio of propionaldehyde to formaldehyde between 1:1.2 mol and 1:0.8 mol. Overall, the feed into reactor 1 including the aqueous phase from process step 2 and the optional recycling stream from the column contains preferably between 1 and 3 mol and more preferably between 1 and 1.5 mol of acid, based on one mole of organic base. These figures are naturally based on acid equivalents and not on molar equivalents. This has to be taken into account in the case of use of diacids such as sulphuric acid in particular.

Preferably, the water content in the overall feed to reactor 1 is greater than 50% by weight and not more than 85% by weight. Equally preferably, the amount of organic base, preferably a secondary amine, for example dimethylamine, in the feed to the reactor comprising the pure base and the particular proportion of base in the salts with the acids and in the base-containing intermediates of process step 1, based on propionaldehyde, is 0.1 to 20 mol %, preferably more than 2 mol %, more preferably more than 5 mol %. Correspondingly, the reaction in that case is conducted with 0.1 to 20 mol %, preferably more than 2 mol % and more preferably at least 5 mol % of acid or the corresponding proportions of acid in the salts with the base.

More particularly, preferably at least 20% of the total amount of organic base in the overall feed comes from a fresh feed. The rest is then fed in by means of the recycling stream from the column bottom.

In general, the process parameters of process step 1 are set in such a way that the methacrolein concentration of the reaction mixture at the outlet of reactor 1 is between 20% and 45% by weight.

In the preparation of methacrolein from propanal and formaldehyde, the reaction mixture—as described—is then fed to a column and stripped therein, preferably with steam. The methacrolein leaves the column overhead together with water. The mixture is condensed and preferably separated by means of a phase separator, especially a phase separation vessel, into an upper phase and a lower phase. The upper phase comprises the methacrolein and is passed onward directly or via optional further purification apparatuses into the reactor of process step 2. The lower phase consists principally of water. It is preferably—as already described—recycled at least partly back into the column for removal of the methacrolein still dissolved therein.

In general, a condenser is also present between the distillation column and the phase separator.

The water content of the crude methacrolein from the distillation can vary as a function of temperature. Preferably, the reaction mixture obtained after the reaction of formaldehyde with propanal is accordingly cooled to a temperature at which the water content in the methacrolein phase is established. Preferably, the temperature in the phase separator can be set between 0 and 50° C., preferably 5 to 30° C. and more preferably 10 to 25° C.

The aqueous catalyst solution can be drawn off at the bottom of the column together with the water formed in the reaction and the water from the formaldehyde solution used. For the further processing, the bottoms liquid can be discarded partly or wholly, batchwise or continuously. More particularly, it is possible to divide the bottoms output into two substreams such that one substream carries precisely the amount of water which has been formed in the reaction and introduced with the starting materials.

This substream is then discharged and the remaining proportion is recycled into the reactor. Aqueous formaldehyde and propanal can also be preheated separately and fed to the reactor.

EXAMPLES

A formalin solution having a formaldehyde content of 37% by weight and propionaldehyde were mixed (referred to below as aldehyde solution) and the mixture was subsequently heated to the desired temperature (see Tab. 1) in an oil-heated heat exchanger. A catalyst solution which contained acetic acid (or retentate or raffinate or mixtures) and dimethylamine (as a 40% by weight solution in water) was likewise preheated to the desired temperature of 160° C. The preheated aldehyde solution and the preheated catalyst solution were then mixed in a static mixer. This reactant mixture was then fed to an oil-heated tubular reactor (⅛" coil, 6 m; ID 1.44, reactor volume 10.1 ml). The reaction was conducted at a pressure of 55 bar. The residence time in the reactor was between 9.4 and 9.7 s. The product mixture at the outflow of the tubular reactor was decompressed via a valve and passed into the product column for distillation. At the top of this column, after condensation and phase separation, a biphasic mixture of methacrolein and an aqueous phase was obtained. This mixture was analysed by means of GC analysis (Varian CP 3800, column: DB Wax, detectors: WLD and FID). Further analysis was effected by means of HPLC analysis; instrument: Agilent 1200, columns: Agilent SB-Aq, UV detector.

Example 1

For the catalyst solution, rather than acetic acid (comparative examples), the retentate from a two-stage membrane system was used. For this purpose, the quench liquid obtained after process step 2 was extracted and the wastewater thus obtained (composition determined by means of HPLC analysis: 2.7% by weight of acetic acid; 0.1% by weight of formic acid; 0.2% by weight of maleic acid; 0.007% by weight of acrylic acid; 0.6% by weight of methacrylic acid; 0.02% by weight of phthalic acid; 0.03% by weight of isophthalic acid; 0.004% by weight of methyl methacrylate; 0.02% by weight of benzoic acid; 0.005% by weight of DiMAL acid (oxidation product of dimeric methacrolein); 0.02% by weight of terephthalic acid) was concentrated in a two-stage membrane system (stage 1 membrane, Duplex NF, Filmtec SW30H, SuS251 L module; stage 2 membrane, PCS-NF, Filmtech SW 30, 240 cm² flat membrane). As fresh feed, 0.8-0.9 kg/h of wastewater was metered in. In this case, a temperature of 30° C. was chosen and a pressure of 80 bar for the first stage was chosen. Stage 2 was likewise operated at 30° C., but at 50 bar. The retentate obtained by membrane had the following composition: 6.4% by weight of acetic acid; 0.5% by weight of formic acid; 0.6% by weight of maleic acid; 0.21% by weight of acrylic acid; 1.5% by weight of methacrylic acid; 0.05% by weight of phthalic acid; 0.07% by weight of isophthalic acid; 0.009% by weight of methyl methacrylate; 0.05% by weight of benzoic acid; 0.01% by weight of DiMAL acid (oxidation product of dimeric methacrolein); 0.05% by weight of terephthalic acid (determined by means of HPLC analysis). In this case, the different acids were regarded as acetic acid equivalents.

This retentate was mixed with DMA and used as catalyst solution according to the procedure described. The conditions and yields are listed in Table 1.

It was found that, surprisingly, the retentate is suitable as substitute for acetic acid. As a result, it was possible to achieve high yields.

Example 2

In a further experiment, a mixture of retentate (for composition see Example 1) and pure acetic acid was used. The starting weights were chosen such that the acetic acid was replaced by the retentate to an extent of 40 mol % acid equivalent. The experimental conditions were chosen as in the preceding example and the experiment was conducted analogously.

Example 3

Here, the raffinate from the extraction was used for the catalyst solution prepared. The wastewater obtained after the extraction was not treated and was used directly for this experiment. The experimental conditions were set analogously to the preceding examples and the experiment was conducted analogously.

Example 4

Finally, the quench liquid was used as catalyst substitute. This contains an even higher proportion of methacrylic acid. The exact composition of the quench liquid used was as follows:

2.7% by weight of acetic acid; 0.15% by weight of formic acid; 0.26% by weight of maleic acid; 0.14% by weight of acrylic acid; 33.0% by weight of methacrylic acid; 0.02% by weight of phthalic acid; 0.03% by weight of isophthalic acid; 0.01% by weight of methyl methacrylate; 0.07% by weight of benzoic acid; 0.01% by weight of DiMAL acid; 0.05% by weight of terephthalic acid; 0.009% by weight of 4-methylbenzoic acid (determined by means of HPLC analysis).

The experimental conditions were chosen as in the preceding example and the experiment was conducted analogously.

Comparative Example 1

The catalyst solution was made up by means of pure acetic acid (glacial acetic acid). The experimental conditions were chosen as in Examples 1 to 4 and the experiment was conducted analogously.

Comparative Example 2

The catalyst solution was made up by means of pure acetic acid (glacial acetic acid). The experimental conditions were chosen as in Examples 1 to 4. Rather than a ⅛" capillary, a plate heat exchanger from IMM having the same reactor volume (10.1 ml) was used.

A further increase in yield can be assumed, since methacrylic acid was detectable in methacrolein. The latter is fed to the oxidation and contributes to an increase in the overall yield therein.

TABLE 1

| | Conditions for the methacrolein synthesis; conversion and | | | | | | |
|---|---|---|---|---|---|---|---|
| selectivity | Propionaldehyde/ formaldehyde [mol/mol] | Dimethylamine/ propionaldehyde [mol/mol] | Dimethylamine/ acetic acid (equivalents) [mol/mol] | Reaction temperature [° C.] | Conversion (propionaldehyde) [%] | Selectivity (methacrolein) [%] | Yield [%] |
| Example 1 | 1.00 | 0.054 | 0.91 | 160 | 98.9 | 98.5 | 97.4 |
| Example 2 | 1.00 | 0.054 | 0.89 | 160 | 99.6 | 98.4 | 98.0 |
| Example 3 | 1.00 | 0.053 | 0.91 | 160 | 99.0 | 98.5 | 97.5 |
| Example 4 | 1.00 | 0.056 | 0.89 | 160 | 99.8 | 98.5 | 98.3 |
| Comparative Example 1 | 1.00 | 0.052 | 0.90 | 160 | 99.7 | 98.2 | 98.0 |
| Comparative Example 2 | 1.00 | 0.042 | 0.91 | 160 | 99.5 | 97.4 | 96.9 |

The invention claimed is:

1. A process for continuously preparing methacrylic acid, comprising:
 a first process step comprising preparing methacrolein from formaldehyde and propionaldehyde with at least one acid and at least one organic base as catalysts in a reactor 1 to obtain a converted reaction solution comprising methacrolein and a catalyst-containing aqueous phase, then
 a second process step comprising:
  separating methacrolein from the catalyst-containing aqueous phase and oxidizing the methacrolein to methacrylic acid with a heterogeneous catalyst in the presence of oxygen and water in a reactor 2, to obtain a process gas, then
  condensing and quenching the process gas to produce an aqueous crude methacrylic acid, and then
  separating the methacrylic acid from an aqueous phase of the aqueous crude methacrylic acid with an extractant to obtain an extracted aqueous phase comprising carboxylic acids, and
  recycling the extracted aqueous phase into reactor 1.

2. The process according to claim 1, wherein the organic base is a secondary amine, and the acid which is fed fresh to reactor 1 is sulphuric acid, formic acid, acetic acid, propionic acid and/or mixtures of these acids.

3. The process according to claim 1, wherein the carboxylic acids present in the aqueous phase passed from the second process step into reactor 1 are acetic acid, methacrylic acid, propionic acid, maleic acid, acrylic acid, terephthalic acid or mixtures comprising at least one of these acids.

4. The process according to claim 1, wherein at least 5% by weight of the acid fed into reactor 1 as catalyst is the carboxylic acids from the second process step.

5. The process according to claim 1, wherein the aqueous phase from the second process step after being extracted and before being introduced into reactor 1 is concentrated by distillation or a membrane separation stage.

6. The process according to claim 1, wherein the converted reaction solution from the first process step after being withdrawn at an exit of the first reactor is distilled in a column and then the methacrolein is separated in a phase separation vessel from the catalyst-containing aqueous phase that separates out, said catalyst-containing aqueous phase being returned wholly or partly to the column.

7. The process according to claim 1, wherein the converted reaction solution from the first process step after being withdrawn at an exit of the first reactor is distilled in a column, and a top stream from the distillation is subsequently passed directly into reactor 2.

8. The process according to claim 6, wherein at least 20% by weight of the catalyst-containing aqueous phase is recycled from bottoms of the column, wherein the bottoms comprising acids and organic bases of the first process step is recycled into the inlet of reactor 1.

9. The process according to claim 1, wherein the aqueous phase from the second process step is passed directly into reactor 1.

10. The process according to claim 8, wherein the aqueous phase from the second process step is passed into the column and thence at least partly into reactor 1 together with the column bottoms.

11. The process according to claim 10, wherein the column bottoms before being introduced into reactor 1 are concentrated by distillation or a membrane separation stage.

12. The process according to claim 7, wherein the aqueous phase from the second process step, before being introduced into reactor 1, is mixed with at least a portion of bottoms from the column and a resulting mixture is optionally concentrated by distillation or a membrane separation stage.

13. The process according to claim 6, wherein a feed into reactor 1 has a ratio of propionaldehyde to formaldehyde between 1:1.2 mol and 1:0.8 mol and, including the aqueous phase from the second process step and an optional recycling stream from the column, contains between 1 and 3 mol of acid based on one mole of organic base.

14. The process according to claim 1, wherein a water content in a feed to reactor 1 is greater than 50% by weight and not more than 85% by weight, an amount of organic base in the feed to the reactor 1, based on propionaldehyde, is more than 2 mol % and a residence time of the reaction mixture in reactor 1 is between 1 and 30 s.

15. The process according to claim 1, wherein pure acetic acid is not passed into reactor 1 after the second process step.

* * * * *